US009204643B2

(12) United States Patent
Hopkins

(10) Patent No.: US 9,204,643 B2
(45) Date of Patent: Dec. 8, 2015

(54) TEMPERATURE STABLE CLOQUINTOCET-MEXYL AQUEOUS COMPOSITIONS

(71) Applicant: Dow AgroSciences LLC, Indianapolis, IN (US)

(72) Inventor: Derek J. Hopkins, New Plymouth (NZ)

(73) Assignee: Dow AgroSciences LLC, Indianapolis, IN (US)

( * ) Notice: Subject to any disclaimer, the term of this patent is extended or adjusted under 35 U.S.C. 154(b) by 165 days.

(21) Appl. No.: 14/134,592

(22) Filed: Dec. 19, 2013

(65) Prior Publication Data

US 2014/0179526 A1  Jun. 26, 2014

Related U.S. Application Data

(60) Provisional application No. 61/745,110, filed on Dec. 21, 2012.

(51) Int. Cl.
| | | |
|---|---|---|
| *A01N 43/42* | (2006.01) | |
| *A01N 43/40* | (2006.01) | |
| *A01N 43/90* | (2006.01) | |
| *A01N 43/36* | (2006.01) | |
| *A01N 25/04* | (2006.01) | |
| *A01N 25/30* | (2006.01) | |

(52) U.S. Cl.
CPC ........................... *A01N 43/42* (2013.01)

(58) Field of Classification Search
CPC ....... A01N 43/42; A01N 43/40; A01N 25/04; A01N 25/30; A01N 43/90; A01N 47/36
See application file for complete search history.

(56) References Cited

U.S. PATENT DOCUMENTS

| | | | |
|---|---|---|---|
| 4,881,966 A | 11/1989 | Nyffeler et al. | |
| 4,902,340 A | 2/1990 | Hubele | |
| 6,479,432 B1 | 11/2002 | Sixl | |
| 6,849,575 B2 | 2/2005 | Haesslin et al. | |
| 7,314,849 B2 | 1/2008 | Balko et al. | |
| 7,432,227 B2 | 10/2008 | Balko et al. | |
| 2002/0055435 A1 | 5/2002 | Baltruschat et al. | |
| 2003/0050194 A1 | 3/2003 | Fowler et al. | |
| 2004/0102321 A1 | 5/2004 | Feucht et al. | |
| 2005/0043182 A1 | 2/2005 | Douglass et al. | |
| 2006/0167018 A1 | 7/2006 | Zagar et al. | |
| 2008/0032890 A1 | 2/2008 | Jensen et al. | |
| 2008/0058209 A1 | 3/2008 | Jensen et al. | |
| 2008/0153704 A1 | 6/2008 | Yamaji et al. | |
| 2008/0248955 A1 * | 10/2008 | Fowler et al. | ............... 504/105 |
| 2010/0016158 A1 | 1/2010 | Kilian et al. | |
| 2010/0190794 A1 | 7/2010 | Hupe et al. | |
| 2010/0279862 A1 | 11/2010 | Bickers et al. | |
| 2010/0285959 A1 | 11/2010 | Armel et al. | |
| 2011/0092367 A1 | 4/2011 | Griveau et al. | |
| 2011/0287932 A1 | 11/2011 | Hacker et al. | |
| 2012/0053053 A1 | 3/2012 | Abdelouahab et al. | |
| 2012/0058899 A1 | 3/2012 | Jensen et al. | |
| 2012/0108424 A1 | 5/2012 | Wu et al. | |

FOREIGN PATENT DOCUMENTS

| | | |
|---|---|---|
| CA | 1218994 | 3/1987 |
| EP | 0094349 | 4/1994 |
| EP | 1306007 | 5/2003 |
| EP | 0795269 | 7/2003 |
| EP | 1313369 | 6/2005 |
| EP | 1347681 | 2/2006 |
| EP | 1423001 | 11/2011 |
| WO | 0234048 | 5/2002 |
| WO | 0236566 | 5/2002 |
| WO | 02045507 | 12/2002 |
| WO | 03022049 | 3/2003 |
| WO | 2005048706 | 11/2005 |
| WO | 2007027863 | 9/2007 |
| WO | 2007067472 | 1/2008 |
| WO | 2008013904 | 1/2008 |
| WO | 2008108973 | 9/2008 |
| WO | 2010009819 | 1/2010 |
| WO | 2010059680 | 8/2011 |
| WO | 2011151247 | 3/2012 |
| WO | 2013026811 | 2/2013 |

OTHER PUBLICATIONS

International Search Report and Written Opinion, dated Aug. 12, 2014, in corresponding International Application No. PCT/US2013/07668, (11 pages).
Farm Chemical International, Crop Protection Database, "Cloquintocet-mexyl," available at http://www.farmchemicalsinternational.com/crop-protection-database/#/product/detail/1450186/ (accessed on May 28, 2014).
Tomlin, C. D. S., Ed., The Pesticide Manual: A World Compendium, "Cloquintocet-mexyl," 15th ed., BCPC: Alton, 2009, pp. 226-227

* cited by examiner

*Primary Examiner* — Abigail Fisher
*Assistant Examiner* — Jessica Kassa
(74) *Attorney, Agent, or Firm* — Michael J. Terapane; Meunier Carlin & Curfman LLC

(57) ABSTRACT

Temperature stable aqueous compositions and methods for their preparation and use are described. The compositions can include cloquintocet-mexyl, a surfactant comprising a tallowamine alkoxylate, a cocoamine alkoxylate, or a combination thereof, and water.

20 Claims, No Drawings

TEMPERATURE STABLE CLOQUINTOCET-MEXYL AQUEOUS COMPOSITIONS

CROSS REFERENCE TO RELATED APPLICATIONS

This application claims the benefit of U.S. Provisional Patent Application Ser. No. 61/745,110 filed Dec. 21, 2012, the disclosure of which is expressly incorporated herein by reference

BACKGROUND

Cloquintocet-mexyl (CQCM) is a safener used with herbicides to reduce phytotoxicity to crops. Suspension concentrate formulations of aqueous cloquintocet-mexyl dispersions are desirable for applying a herbicide and safener mixture to crops. When formulated in an aqueous environment, cloquintocet-mexyl is hydrated and forms needle-shaped crystals. These hydrated cloquintocet-mexyl suspension concentrate formulations can be unstable upon storage at temperatures of 25° C. and greater, resulting in gross crystal growth and flocculation. Furthermore, non-aqueous cloquintocet-mexyl formulations, such as oil dispersions and water dispersible granules, have limited loading capabilities, higher manufacturing costs, and mediocre dilution properties and tank mix compatibilities.

SUMMARY

Temperature stable aqueous hydrated cloquintocet-mexyl suspension compositions and methods for their preparation and use are described. The temperature stable aqueous compositions include hydrated cloquintocet-mexyl, a stabilizing surfactant, and water. The stabilizing surfactant includes a tallowamine alkoxylate, a cocoamine alkoxylate, or a combination thereof. In some embodiments, the surfactant is ethoxylated. The surfactant can include an average of from 10 to 20 moles of ethylene oxide (e.g., an average of from 12 to 15 moles of ethylene oxide). The composition can be a suspension concentrate.

The composition can further include a pesticide. The pesticide can be selected from the group consisting of clodinafop-propargyl, flupyrsulfuron, pyroxsulam, and 4-aminopicolinic acid based herbicides. In some embodiments, the weight ratio of hydrated cloquintocet-mexyl to the pesticide is from 1:1 to 9:1. In some embodiments, the composition comprises from 150 g/L to 225 g/L of hydrated cloquintocet-mexyl.

In some embodiments, the composition can further include one or more additional surfactants, such as wetting surfactants. The one or more additional surfactants can be optionally added to the composition to aid the physical stability and dispersion of the compositions.

Also described is a method of reducing crystal growth of an aqueous suspension of hydrated cloquintocet-mexyl. The method can include contacting an aqueous suspension of hydrated cloquintocet-mexyl with a surfactant selected from the group consisting of a tallowamine alkoxylate, a cocoamine alkoxylate, and mixtures thereof, to produce a stabilized composition. A method of stabilizing an aqueous suspension of hydrated cloquintocet-mexyl is also described. The method can include contacting an aqueous suspension of hydrated cloquintocet-mexyl with a surfactant selected from the group consisting of a tallowamine alkoxylate, a cocoamine alkoxylate, and mixtures thereof to form a stabilized composition, wherein the stabilized composition is stable at a temperature of 30° C. or greater. In the methods described herein, the stabilized composition can be stable at a temperature of from 30° C. to 45° C. In some embodiments, the stabilized composition can be stable at an elevated temperature for at least one year.

Further described herein is a method of making a stabilized aqueous composition of hydrated cloquintocet-mexyl. The method can include mixing anhydrous cloquintocet-mexyl with an aqueous composition comprising water and a wetting surfactant to form an aqueous hydrated cloquintocet-mexyl composition, converting at least 95% of the anhydrous cloquintocet-mexyl to hydrated cloquintocet-mexyl; mixing a stabilizing surfactant comprising a tallowamine alkoxylate, a cocoamine alkoxylate, or a combination thereof with the aqueous hydrated cloquintocet-mexyl composition; and milling the resultant product.

The details of one or more embodiments are set forth in the description below. Other features, objects, and advantages will be apparent from the description and from the claims.

DETAILED DESCRIPTION

Temperature stable aqueous suspension compositions containing hydrated cloquintocet-mexyl (CQCM) and methods for their preparation are described herein. The compositions include cloquintocet-mexyl, a surfactant, and water. The surfactant includes a tallowamine alkoxylate, a cocoamine alkoxylate, or a combination thereof.

Cloquintocet-mexyl is a safener applied in combination with pesticides and is useful for reducing phytotoxicity to crops such as rice, cereal, and wheat. In some embodiments, cloquintocet-mexyl acts as an antidote or antagonist in the crop and can reduce or prevent damage to the crop. Cloquintocet-mexyl can be mixed with water to form an aqueous dispersion. When mixed with water, cloquintocet-mexyl is hydrated thereby resulting in a hydrated cloquintocet-mexyl structure. As used herein, hydrated cloquintocet-mexyl refers to the structure where at least 95% of the anhydrous cloquintocet-mexyl is hydrated. For example, at least 96%, at least 97%, at least 98%, or at least 99% (e.g., 100%) of the anhydrous cloquintocet-mexyl can be hydrated to form a hydrated cloquinocet-mexyl. The hydrated structure can be in the form of needle-shaped crystals.

As described above, the composition further includes a surfactant that stabilizes the hydrated cloquintocet-mexyl structure. The surfactant (i.e., stabilizing surfactant) as described herein can include a tallowamine alkoxylate, a cocoamine alkoxylate, or a combination of these. In some embodiments, the tallowamine alkoxylate is a tallow monoamine alkoxylate. In some embodiments, the cocoamine alkoxylate is a cocomonoamine alkoxylate. Suitable tallowamine alkoxylates and cocoamine alkoxylates include ETHOMEEN T/25, T/15, and C/12 surfactants commercially available from Akzo Nobel; Amsterdam, The Netherlands. Optionally, the stabilizing surfactant can be ethoxylated. In some embodiments, the stabilizing surfactant can comprise an average of up to 30 moles of ethylene oxide (e.g., an average of from 2 moles to 25 moles, from 5 moles to 23 moles, from 10 to 20 moles, or from 12 to 15 moles) per mole of surfactant. For example, the stabilizing surfactant can comprise an average of 1 mol of ethylene oxide, 2 moles of ethylene oxide, 3 moles of ethylene oxide, 4 moles of ethylene oxide, 5 moles of ethylene oxide, 6 moles of ethylene oxide, 7 moles of ethylene oxide, 8 moles of ethylene oxide, 9 moles of ethylene oxide, 10 moles of ethylene oxide, 11 moles of ethylene oxide, 12 moles of ethylene oxide, 13 moles of ethylene oxide, 14 moles of ethylene oxide, 15 moles of ethylene oxide, 16 moles of ethylene oxide, 17 moles of ethylene oxide, 18 moles of ethylene oxide, 19 moles of ethylene oxide, 20 moles of ethylene oxide, 21 moles of ethylene oxide, 22 moles of ethylene oxide, 23 moles of ethylene oxide, 24 moles of ethylene oxide, 25 moles of ethylene oxide, 26 moles of ethylene oxide, 27 moles of ethylene oxide, 28 moles of ethylene oxide, or 29 moles of ethylene oxide.

The composition can further include one or more additional surfactants, such as wetting surfactants. The one or more additional surfactants can be optionally added to the composition to aid the physical stability and dispersion of the hydrated cloquintocet-mexyl in the compositions. Exemplary additional surfactants include, but are not limited to, the alkali metal salts, alkaline earth metal salts and ammonium salts of: aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ethers, alkyl aryl polyether alcohols, isotridecyl alcohol and fatty alcohol/ethylene oxide condensates, ethoxylated castor oil, polyoxyethylene alkyl ethers or polyoxypropylene alkyl ethers, lauryl alcohol polyglycol ether acetates, sorbitol esters, lignosulfite waste liquors and proteins, denatured proteins, polysaccharides (e.g., methylcellulose), hydrophobically modified starches, polyvinyl alcohols, polycarboxylates, polyalkoxylates, polyvinyl amines, polyethyleneimines, polyvinylpyrrolidones, and copolymers thereof. In some embodiments, the additional surfactant includes a naphthalenesulfonic acid salt such as MORWET D-425, commercially available from Akzo Nobel.

The composition described herein can further comprise a pesticide. The pesticides for inclusion in the compositions described herein can include, for example, clodinafop-propargyl, flupyrsulfuron, pyroxsulam, or 4-aminopicolinic acid based herbicides. Examples of 4-aminopicolinic acid based herbicides, including halauxifen and halauxifen-methyl, are described in U.S. Pat. Nos. 7,314,849 and 7,432,227 to Balko et al., which are hereby incorporated by reference in their entireties. In certain embodiments, the composition described herein can further comprise pyroxsulam. Additional exemplary pesticides suitable for use in the compositions described herein include 2,4-D, acetochlor, aclonifen, amicarbazone, ametryn, amidosulfuron, aminopyralid, aminocyclopyrachlor, aminotriazole, ammonium thiocyanate, asulam, anilofos, atrazine, beflubutamid, benazolin, bentazone, bifenox, bromacil, bromoxynil, butachlor, butafenacil, butralin, butroxydim, carbetamide, carfentrazone, carfentrazone-ethyl, chlormequat, chlorsulfuron, chlortoluron, cinidon-ethyl, clethodim, clomazone, cyanazine, cyclosulfamuron, cycloxydim, dicamba, dichlobenil, dichlorprop, dichlorprop-P, diclofop-methyl, diclosulam, diflufenican, diflufenzopyr, dimefuron, dimethachlor, diquat, diuron, EPTC, ethoxysulfuron, fenoxaprop, fenoxaprop-ethyl, fenoxaprop-ethyl+isoxadifen-ethyl, fenoxaprop-P-ethyl, fenoxsulfone, flazasulfuron, florasulam, fluazifop, fluazifop-P-butyl, flucarbazone, flucarbazone-sodium, flucetosulfuron (LGC-42153), flufenacet, flumetsulam, flumioxazin, fluroxypyr, fluroxypyr-meptyl, flurtamone, gibberellic acid, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop, mecoprop-P, mesosulfuron, mesosulfuron-ethyl sodium, metazochlor, metosulam, metribuzin, metsulfuron, metsulfuron-methyl, MSMA, 1-napthaleneacetic acid, napropamide, nopropamide-M, norfurazon, orthosulfamuron, oryzalin, oxadiargyl, oxadiazon, oxyfluorfen, paraquat, pendimethalin, penoxsulam, picloram, picolinafen, pinoxaden, piperophos, primisulfuron, profluazol, prometon, propanil, propaquizafop, propoxycarbazone, propyzamide, prosulfocarb, prosulfuron, pyraflufen-ethyl (ET-751), pyrasulfotole, pyribenzoxim (LGC-40863), pyroxasulfone, quinclorac, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxidim, terbacil, terbutryn, thiazopyr, thiencarbazone-methyl, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof.

In compositions containing a pesticide, the weight ratio of hydrated cloquintocet-mexyl to the pesticide can be from 1:1 to 9:1. For example, the weight ratio of hydrated cloquintocet-mexyl to the pesticide can be 1.5:1, 2:1, 2.5:1, 3:1, 3.5:1, 4:1, 4.5:1, 5:1, 5.5:1, 6:1, 6.5:1, 7:1, 7.5:1, 8:1, or 8.5:1. The composition can include from 150 g/L to 225 g/L of hydrated cloquintocet-mexyl. For example, the composition can include from 160 g/L to 220 g/L, 170 g/L to 210 g/L, or 180 g/L to 200 g/L of hydrated cloquintocet-mexyl.

Optionally, the compositions described herein can include one or more additives. The additives can include an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, spreading agents, dispersing agents, thickening agents, freeze point depressants, antimicrobial agents, crop oil, safeners, adhesives (for instance, for use in seed formulations), protective colloids, emulsifiers, tackifiers, and mixtures thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamin B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof.

The additive can also include a solid filler. Exemplary solid fillers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

The compositions described herein can be in the form of an aqueous suspension concentrate (SC). As used herein, suspension concentrate refers to a stable suspension of one or more active ingredients in an aqueous phase. The performance characteristics of the suspension concentrate can be determined by using methods as known to those of skill in the art, including pourability, water dispersibility, suspensibility, particle size, wet sieve analysis, and viscosity tests.

A method of making a stabilized aqueous composition of hydrated cloquintocet-mexyl is also described herein. The method can include mixing anhydrous cloquintocet-mexyl with an aqueous composition comprising water and a wetting surfactant to form an aqueous hydrated cloquintocet-mexyl composition, converting at least 95% of the anhydrous cloquintocet-mexyl to hydrated cloquintocet-mexyl, mixing a stabilizing surfactant comprising a tallowamine alkoxylate, a cocoamine alkoxylate, or a combination thereof with the aqueous hydrated cloquintocet-mexyl composition, and milling the resultant product.

The mixing steps can be conducted in a mixing apparatus such as a low shear agitator or a high shear agitator. The anhydrous cloquintocet-mexyl can be mixed with water, a wetting surfactant, and one or more additional components until at least 95% of the anhydrous cloquintocet-mexyl is converted to hydrated cloquinocet-mexyl, as described above. In some examples, the components can be mixed for 30 minutes or greater. For example, the components can be mixed for 40 minutes or greater, 50 minutes or greater, 1 hour or greater, or 2 hours or greater. Optionally, the components are mixed using a low shear agitator.

The aqueous hydrated cloquintocet-mexyl composition can then be mixed with a stabilizing surfactant and one or more additional additives as described herein to form a slurry. Optionally, a pesticide as described herein can be combined with the cloquintocet-mexyl, the stabilizing surfactant, the one or more additional additives, or the resulting slurry. The slurry can then be mixed using, for example, a high shear agitator. The resulting mixture can be processed through a mill (e.g., a bead mill) to form the finished product.

Contacting the aqueous suspension of hydrating cloquintocet-mexyl with the stabilizing surfactant as described herein can reduce the crystal growth of the hydrated cloquintocet-mexyl particles in the suspension and stabilize the aqueous suspension, resulting in a stabilized composition. The stabilized compositions can be stable at ambient temperatures and elevated temperatures. Optionally, the stabilized composition can be stable at a temperature of 30° C. or greater, 35° C. or greater, 40° C. or greater, or 45° C. or greater. In some embodiments, the stabilized composition can be stable at a temperature of from 30° C. to 45° C., from 35° C. to 50° C., or from 40° C. to 55° C. The stabilized composition can be stable at the elevated temperature for at least one year (e.g., at least two years, at least three years, at least four years, or at least five years). The resulting stabilized composition can be suitable for applications, including spray applications, after storage.

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (i.e., before the emergence of undesirable vegetation) or post-emergence (i.e., during and/or after emergence of the undesirable vegetation). In some embodiments, the compositions disclosed herein are applied post-emergence when the undesirable vegetation starts with leaf development up to flowering. In some embodiments, the compositions disclosed herein are applied post-emergence to relatively immature undesirable vegetation to achieve the maximum control of weeds. In some embodiments when the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applying to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 1/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, sugar beets; cereals such as wheat and wheat-like crops, rye, triticale and barley, corn, oats, maize, sorghum, rice, and sugar cane; and oilseed crops such as canola, oilseed rape and sunflower; fodder brassicas. In some embodiments, the compositions and methods disclosed herein can be used for controlling undesired vegetation in non-crop areas. Exemplary non-crop areas include, but are not limited to, turf, pasture, fallow, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), aquatics, trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms. The compositions and methods disclosed herein can also be used in crop plants that are resistant to, for instance, herbicides, pathogens, and/or insects.

The examples below are intended to further illustrate certain aspects of the methods and compositions described herein, and are not intended to limit the scope of the claims.

EXAMPLES

Example 1

Evaluation of for Preventing Crystal Growth and Providing Particle Size Stability to Hydrated CQCM (Cloquintocet-Mexyl) Aqueous Suspension Compositions An exemplary hydrated CQCM suspension concentrate composition is shown in Table 1.

TABLE 1

Composition of Hydrated CqCM Suspension Concentrates.

| Material | Amount (% w/w) |
| --- | --- |
| Cloquintocet-mexyl | 5.0 |
| Dispersant | 2.0 |
| Tridecyl alcohol ethoxylate (SYNPERONIC 13/6.5; wetting surfactant) | 0.5 |
| Propylene glycol | 10.0 |
| Poly(dimethylsiloxane) emulsion (Dow Corning ANTIFOAM 1430) | 2.0 |
| Xanthan gum (RHODOPOL 50MD) | 0.15 |
| 1,2-benzisothiazolin-3-one solution (PROXEL GXL) | 0.08 |
| Water | 80.27 |

SYNPERONIC 13/6.5 is a wetting agent commercially available from Croda USA; Edison, N.J. DOW CORNING ANTIFOAM 1430 is an antifoam commercially available from Dow Corning; Midland, Mich. RHODOPOL 50MD is a thickener commercially available from Rhodia; Boulogne-Billancourt, France. PROXEL GXL is a biocide commercially available from Arch Biocides; Smyrna, Ga.

Short term accelerated temperature screening studies were conductted to determine the crystal growth control and stability of hydrated CQCM compositions containing various dispersants (Tables 2 and 3) to identify suitable stabilizing surfactants for hydrated CQCM compositions. Compositions according to Table 1 were prepared using the dispersants listed in Table 2. Short term accelerated temperature stability tests were performed using freeze/thaw (F/T) conditions during which the temperature was cycled between about −10° C. and 40° C. in a 2 hour period after remaining at −10° C. or 40° C. for 24 hours. The compositions were evaluated for hydrated CQCM crystal growth using a microscope and for particle size changes using a laser diffraction particle size analyzer after eight days of storage. The results are shown in Table 2. Particle sizes are reported as the volume mean diameter in microns (μm) as D(0.5) and D(0.9) values.

TABLE 2

Stabilizing Surfactant Screening Study (F/T: −10° C./40° C.; 8 Days)

| Dispersant Evaluated (Tradename) | Initial Particle Size | | Particle Size After Accelerated Storage | | Hydrated CQCM Crystal Growth Observed |
| --- | --- | --- | --- | --- | --- |
| | D(0.5) μm | D(0.9) μm | D(0.5) μm | D(0.9) μm | |
| Tallow amine 15 ethoxylate (ETHOMEEN T/25) | 4.7 | 12.1 | 4.8 | 14.1 | No crystal growth |
| Alkyl naphthalene sulfonate, sodium (MORWET D425) | 5.0 | 13.3 | 5.3 | 15.0 | Minor crystal growth |
| Diamine co-polymer (SYNPERONIC T/908) | 4.7 | 14.3 | 5.6 | 21.9 | Crystal growth |
| Alkoxylated alcohol (WITCONOL 500LQ) | 3.9 | 11.1 | 4.7 | 17.9 | Crystal growth |
| 16 ethoxylate tristyrylphenol phosphate, potassium (SOPROPHOR FLK) | 4.0 | 11.9 | 5.0 | 19.3 | Crystal growth |
| Lignosulphonate, calcium (BORRESPERSE CA) | 3.8 | 14.0 | 4.8 | 20.9 | Crystal growth |
| Tristyrylphenol 16 ethoxylate (SOPROPHOR BSU) | 4.0 | 11.6 | 5.1 | 20.1 | Crystal growth |
| Comb dispersant (ATLOX 4913) | 3.5 | 10.6 | 4.5 | 19.0 | Crystal growth |
| Alkoxylated alcohol (ATLAS G5000) | 3.3 | 10.1 | 4.4 | 17.7 | Crystal growth |
| Alkylated PVP (AGRIMER AL10) | 4.3 | 13.9 | 6.5 | 23.8 | Crystal growth |
| Alkyl polyglucoside (AGRIMUL PG2067) | 4.3 | 14.4 | 6.5 | 36.9 | Crystal growth |
| Polycarboxylate (GEROPON T-36) | 3.9 | 13.9 | 18.8 | 65.4 | Crystal growth |

ETHOMEEN T/25, MORWET D425, and WITCONOL 500LQ are commercially available from Akzo Nobel; Amsterdam, The Netherlands. SYNPERONIC T/908, ATLOX 4913, and ATLAS G5000 are commercially available from Croda USA; Edison, N.J. SOPROPHOR FLK, SOPROPHOR BSU, and GEROPON T-36 are commercially available from Rhodia; Boulogne-Billancourt, France. BORRESPERSE CA is commercially available from Borregaard LignoTech; Sarpsborg, Norway. AGRIMER AL10 is commercially available from Ashland Specialty Ingredients; Wayne, N.J. AGRIMUL PG2067 is commercially available from Henkel Corporation; Dusseldorf, Germany.

Compositions according to Table 1 were prepared using the dispersants listed in Table 3. Short term accelerated temperature stability tests were performed using freeze/thaw (F/T) conditions during which the temperature was cycled between about −10° C. and 40° C. in a 2 hour period after remaining at −10° C. or 40° C. for 24 hours. The compositions were evaluated for hydrated CQCM crystal growth using a microscope and for particle size changes using a laser diffraction particle size analyzer after fourteen days of storage. The results are shown in Table 3. Particle sizes are reported as the volume mean diameter in microns (μm) as D(0.5) and D(0.9) values.

TABLE 3

Stabilizing Surfactant Screening Study (F/T: −10° C./40° C.; 14 Days)

| Dispersant Evaluated (Tradename) | Initial Particle Size | | Particle Size After Accelerated Storage | | Hydrated CQCM Crystal Growth Observed |
|---|---|---|---|---|---|
| | D(0.5) μm | D(0.9) μm | D(0.5) μm | D(0.9) μm | |
| Tallow amine 5 ethoxylate (ETHOMEEN T/15) | 15.1 | 48.4 | 15.3 | 58.4 | No crystal growth |
| Cocoamine 2 ethoxylate (ETHOMEEN C/12) | 12.6 | 35.8 | 14.4 | 39.1 | No crystal growth |
| Hexadecyl trimethyl-ammonium quaternary, chloride (ARQUAD 16-29) | 20.6 | 65.8 | 18.4 | 68.5 | No crystal growth |
| Coco (2 ethoxylate) ammonium quaternary, chloride (ETHOQUAD C/12) | 17.4 | 80.4 | 21.1 | 71.7 | Minor crystal growth |
| Oleyl alcohol 17 ethoxylate (LUBROL 17A17) | 4.7 | 17.8 | 6.8 | 33.3 | Crystal growth |
| Oleyl alcohol 5 ethoxylate (AGNIQUE FOH-181-5) | 3.6 | 10.0 | 5.7 | 72.9 | Crystal growth |
| Oleyl alcohol 7 ethoxylate (AGNIQUE FOH 28-7) | 3.3 | 10.7 | 4.5 | 16.5 | Crystal growth |
| Castor oil 36 ethoxylate (TERMUL 1284) | 3.6 | 11.0 | 4.0 | 14.0 | Crystal growth |

ETHOMEEN T/15 and ETHOMEEN C/12 are commercially available from Akzo Nobel; Amsterdam, The Netherlands. LUBROL 17A17 is commercially available from Croda USA; Edison, N.J. AGNIQUE FOH-181-5 and AGNIQUE FOH 28-7 are commercially available from BASF Corporation; Florham Park, N.J. TERMUL 1284 is commercially available from Huntsman; The Woodlands, Tex.

Example 2

Hydrated CQCM Suspension Concentrate Composition Containing Pyroxsulam

In Example 1, ETHOMEEN T/25 was shown to control crystal growth. MORWET D-425 was shown to provide some crystal growth control as well as to provide favorable dispersion properties to the composition. A hydrated CQCM suspension concentrate composition containing ETHOMEEN C/25 (to control crystal growth) and MORWET D-425 (to provide favorable dispersion properties) was subsequently evaluated.

A hydrated CQCM suspension concentrate composition containing ETHOMEEN C/25, MORWET D-425, and pyroxsulam is shown in Table 4.

TABLE 4

Hydrated CQCM/Pryoxsulam Concentrate Composition.

| Material | Amount (g/L) |
|---|---|
| Pyroxsulam | 50 |
| Cloquintocet-mexyl | 150 |
| Dow Corning ANTIFOAM 1430 | 2 |
| Propylene glycol (antifreeze agent) | 75 |
| PROXEL GXL (biocide) | 0.75 |
| ETHOMEEN C-25 (stabilizing surfactant) | 37.5 |
| MORWET D-425 (dispersant) | 37.5 |
| Citric acid (pH buffer) | 2.5 |
| Veegum (suspending aid) | 10 |
| KELZAN S/RHODOPOL 50MD (thickener) | 1.5 |
| SYNPERONIC 13/6.5 (wetter) | 5 |
| Water | To 1 liter |

The aqueous phase was formed by combining water, propylene glycol, antifoam, and wetter surfactant (SYNPERONIC 13/6.5; Croda USA) in a vessel. Powdered anhydrous CQCM was added to the aqueous phase and mixed with a low shear turbine type agitator for 1 hour or until the CQCM was fully converted to the hydrate. A tallow or coco-amine 15 mole ethoxylate (e.g., ETHOMEEN C-25; Akzo Nobel), and MORWET D-425 (Akzo Nobel) were added and mixed in with high shear agitation, followed by the addition of the remaining ingredients shown in Table 4. KELZAN S is a thickener commercially available from CPKelco; Atlanta, Ga. The slurry was then processed through a bead mill to yield the finished product. Short term accelerated storage testing was conducted using freeze/thaw (F/T) conditions during which the temperature was cycled between about −10° C. and 40° C. in a 2 hour period after remaining at −10° C. or 40° C. for 24 hours, as in Example 1. Samples of the composition containing pyroxsulam were also stored for two weeks at 54° C. to evaluate chemical stability of the CQCM and. The stability results are shown in Table 5.

TABLE 5

Storage Stability of Hydrated CQCM/Pyroxsulam Concentrate.

| | Storage Conditions | | |
|---|---|---|---|
| Property | Initial Composition | −10° C./40° C. Cycling (8 Days) | 54° C. (2 Weeks) |
| Appearance | Homogenous, free-flowing liquid free of sediment | Homogenous, free-flowing liquid free of sediment | Homogenous, paste-like solid, free of sediment |
| Persistent foam (% v/v) | 0 | 0 | — |

TABLE 5-continued

Storage Stability of Hydrated CQCM/Pyroxsulam Concentrate.

| Property | Storage Conditions | | |
|---|---|---|---|
| | Initial Composition | −10° C./ 40° C. Cycling (8 Days) | 54° C. (2 Weeks) |
| Wet Sieve (75 µm, % retained) | 0 | 0 | — |
| Particle Size - D(0.5) (µm) | 2.7 | 2.8 | — |
| Particle Size - D(0.9) (µm) | 10.6 | 11.2 | — |
| pH (neat) | 7.0 | 6.9 | — |
| Density (at 20° C.) (g/mL) | 1.073 | 1.073 | — |
| Viscosity (at 20° C.) (mPas) | 23 | 26 | — |
| Chemical Analysis (% w/w) | | | |
| Pyroxsulam | 4.65 | — | 4.73 |
| CQCM | 13.69 | — | 13.24 |
| Chemical Stability (%) | | | |
| Pyroxsulam | — | — | 102 |
| CQCM | — | — | 97 |

A 10 L production batch of the composition shown in Table 4 was prepared, dispatched for field trials in Australia, and stored for 1 year in an unheated shed subjected to temperatures ranging from −4° C. to 43° C. The 1 year sample showed no change in properties compared to the retainer sample of the initially prepared composition (see Table 6).

TABLE 6

One Year Storage Stability of Hydrated CQCM/Pyroxsulam Concentrate

| Test Item | Initial | After 1 year |
|---|---|---|
| Density | 1.08 g/mL | 1.08 g/mL |
| pH | 6.05 | 6.21 |
| Particle Size | D(0.5): 3.05 µm D(0.9): 11.89 µm | D(0.5): 2.59 µm D(0.9): 11.79 µm |
| Chemical Stability | Content (% w/w) Pyroxsulam: 4.65 CQCM: 14.15 | Content (% w/w) Pyroxsulam: 4.84 CQCM: 14.40 Retention (%) Pyroxsulam: 104 CQCM: 102 |
| Syneresis | no top cleaning | 3% top cleaning no sedimentation |
| Viscosity (at 20° C.) | 27 mPas (Herschel Bulkley) | 17 mPas (Herschel Bulkley) |
| Spontaneity (Bloom) | | 85% |
| Wet sieve (75 µm, % retained) | | <0.1% |
| Persistent Foaming | 0% | 0% |

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative composition materials and method steps disclosed herein are specifically described, other combinations of the composition materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed.

What is claimed is:

1. A method of reducing crystal growth of an aqueous suspension of hydrated cloquintocet-mexyl, comprising:
   contacting an aqueous suspension of hydrated cloquintocet-mexyl with a surfactant selected from the group consisting of a tallowamine alkoxylate, a cocoamine alkoxylate, and mixtures thereof.

2. The method of claim 1, wherein the stabilized composition is stable at a temperature of 30° C. or greater.

3. The method of claim 2, wherein the stabilized composition is stable at a temperature from 30° C. to 45° C.

4. The method of claim 1, wherein the surfactant is ethoxylated.

5. The method of claim 4, wherein the surfactant comprises an average of from 10 to 20 moles of ethylene oxide.

6. The method of claim 1, wherein the stabilized composition further comprises a pesticide, and wherein the pesticide is selected from the group consisting of clodinafop-propargyl, flupyrsulfuron, pyroxsulam, and 4-aminopicolinic acid based herbicides.

7. The method of claim 1, wherein the stabilized composition comprises from 150 g/L to 225 g/L of hydrated cloquintocet-mexyl.

8. The method of claim 7, wherein the weight ratio of hydrated cloquintocet-mexyl to the pesticide is from 1:1 to 9:1.

9. A method of making a stabilized aqueous composition of hydrated cloquintocet-mexyl, comprising:
   mixing anhydrous cloquintocet-mexyl with an aqueous composition comprising water and a wetting surfactant to form an aqueous cloquintocet-mexyl composition;
   converting at least 95% of the anhydrous cloquintocet-mexyl to hydrated cloquintocet-mexyl;
   mixing a stabilizing surfactant comprising a tallowamine alkoxylate, a cocoamine alkoxylate, or a combination thereof with the aqueous hydrated cloquintocet-mexyl composition; and
   milling the resultant product; wherein the stabilizing surfactant reduces the crystal growth of the hydrated cloquintocet-mexyl resulting a stabilized composition.

10. The method of claim 9, wherein the stabilizing surfactant is ethoxylated.

11. The method of claim 10, wherein the stabilizing surfactant comprises an average of from 10 to 20 moles of ethylene oxide.

12. The method of claim 9, wherein a pesticide is combined with the resultant product, and wherein the pesticide is selected from the group consisting of clodinafop-propargyl, flupyrsulfuron, pyroxsulam, and 4-aminopicolinic acid based herbicides.

13. The method of claim 12, wherein the weight ratio of hydrated cloquintocet-mexyl to the pesticide is from 1:1 to 9:1.

14. The method of claim 9, wherein the stabilized composition comprises from 150 g/L to 225 g/L of hydrated cloquintocet-mexyl.

15. A temperature stable aqueous composition comprising:
    hydrated cloquintocet-mexyl;
    a surfactant comprising a tallowamine alkoxylate, a cocoamine alkoxylate, or a combination thereof; and
    water; wherein the stabilizing surfactant reduces the crystal growth of the hydrated cloquintocet-mexyl resulting a stabilized composition.

16. The composition of claim 15, wherein the surfactant is ethoxylated.

17. The composition of claim 16, wherein the surfactant comprises an average of from 10 to 20 moles of ethylene oxide.

18. The composition of claim 15, further comprising a pesticide, wherein the pesticide is selected from the group consisting of clodinafop-propargyl, flupyrsulfuron, pyroxsulam, and 4-aminopicolinic acid based herbicides.

19. The composition of claim 18, wherein the weight ratio of hydrated cloquintocet-mexyl to the pesticide is from 1:1 to 9:1.

20. The composition of claim 15, wherein the composition comprises from 150 g/L to 225 g/L of hydrated cloquintocet-mexyl.

* * * * *